United States Patent [19]

Meyer et al.

[11] 4,440,561
[45] Apr. 3, 1984

[54] DEFOLIANT COMPOSITION AND METHOD

[75] Inventors: Jacques Meyer, Zofingen; Walter E. Schären, Vordemwald, both of Switzerland

[73] Assignee: Siegfried Aktiengesellschaft, Zofingen, Switzerland

[21] Appl. No.: 345,490

[22] Filed: Feb. 3, 1982

[30] Foreign Application Priority Data

Feb. 19, 1981 [CH] Switzerland ............... 1101/81

[51] Int. Cl.³ ........................................... A01N 37/40
[52] U.S. Cl. ........................................ 71/70; 71/108; 71/120
[58] Field of Search ........................... 71/108, 120, 70

[56] References Cited

U.S. PATENT DOCUMENTS

| 2,945,753 | 7/1960 | Brugmann et al. | 71/70 |
| 3,079,244 | 2/1963 | Scherer et al. | 71/120 |
| 3,776,715 | 12/1973 | Theissen | 71/111 |
| 4,192,668 | 3/1980 | Phillips | 71/70 |

Primary Examiner—Catherine L. Mills
Attorney, Agent, or Firm—Werner W. Kleeman

[57] ABSTRACT

Compositions containing Bifenox and Linuron in combination with a mineral oil, such as white oil, show a remarkable synergism of the constituents and are of use as pre-harvest defoliants for crop plants, e.g. for desiccation of potato plants.

9 Claims, No Drawings

DEFOLIANT COMPOSITION AND METHOD

BACKGROUND OF THE INVENTION (a) Field of the Invention

The invention relates generally to agrochemical compositions and specifically to compositions and methods for controlled pre-harvest defoliation of crop plants, such as for desiccation of potatoes and the like crop cultures.

(b) Description of the Prior Art

Defoliating agents or defoliants are used in agriculture to control undesirably strong development of crop plant foliage and in order to initiate at an early stage, or to accelerate, normal plant decay including defoliation and/or desiccation of leaves and stems of crop plants which decay is part of the normal vegetation cycle but would take longer without use of such defoliants or desiccants. This is of particular importance for controlled initiation or acceleration of decay and desiccation of crop plant components that preclude, or render difficult, the harvesting operation including use of harvesting machines.

The use of defoliants in Central Europe is of commercial importance mainly in connection with potato cultures. Potato harvest starts when the leaves and overground stem portions dry up or desiccate near the end of the vegetation period, and a delay of desiccation due to anomalies of weather conditions before or at the harvest period may be detrimental in that actual harvest may be complicated or even impossible after commencement of rainy or extremely cold fall period weather. Thus, controlled pre-harvest defoliation or desiccation of the potato plants is desirable so that termination of vegetation can be initiated and controlled essentially independent of climatic conditions.

Approved defoliants or desiccants (also called vine desiccants) used at present in substantial quantities are preparations containing, as active ingredient, 4,6-dinitro-o-kresol ("DNOC"), or 2-sec.-butyl-4,6-dinitrophenol (common name "Dinoseb"), or 1,1'-ethylene-2,2'-bipyridyllium salts (common name "Diquat").

Obviously, both selection as well as admission for use by government authorities of such active ingredients does not only depend upon the actual chemical effectiveness of such substance per se but upon other important parameters, such as toxicity and other characteristics of the active substance under consideration including possible influences upon the environment, chemical decomposition characteristics, the tendency to form residues in the soil, consequences for subsequent crops or "carry-over" and—last but not least—consequences upon the quality of the harvested products.

The three substances mentioned above meet these selection criteria to an extent that is assumed to meet reasonable standards. This does not justify the assumption, however, that these substances or active ingredients are entirely free of problems. For example, those persons that have to handle or apply the agents or compositions find that these substances have rather inconvenient properties and are not entirely free of hazards; for example, both DNOC and Dinoseb cause a penetrating yellow coloration of the skin and Diquat, in concentrated form, can damage the finger nails and cause other irritations.

Accordingly, there is a need to provide for pre-harvest defoliants and methods with the same defoliant effectiveness as the best prior art compositions and methods but without the disadvantages just mentioned.

SUMMARY AND OBJECTS OF THE INVENTION

Accordingly, it is an object of the invention to provide for an improved defoliant composition, notably for controlled pre-harvest defoliation or desiccation of over-ground portions of crop plants, such as potatoes, having a defoliant/desiccant effectiveness similar to the best prior art compositions but without the disadvantages of the latter.

Another object of the invention is to provide for a method of controlled pre-harvest defoliation or desiccation by a combination of substances which has substantially the same defoliant/desiccant effectiveness as optimal prior art agents but which does not have the disadvantages of the prior art substances.

An improved composition which, according to the present knowledge, meets the above objects has been found according to the invention and comprises, according to a first general embodiment a synergistic combination of the following constituents:

(1) methyl-5-(2,4-dichlorophenoxy)-2-nitrobenzoate;

(2) 3-(3,4-dichlorophenyl)-1-methoxy-1-methyl urea, and (3) a mineral oil.

For many uses, the inventive composition further comprises (4) at least one agrochemical emulsifying agent for oily compositions that are applied as aqueous sprays.

According to a second general embodiment, the invention provides for a method of controlled pre-harvest defoliation or desiccation of crop plant foliage and stem materials by applying onto said foliage and stem materials the above mentioned components (1), (2) and (3) in a synergistic combination, preferably by spraying of an aqueous formulation that contains at least one emulsifying agent (4).

DESCRIPTION OF THE INVENTION

Constituent (1) of the inventive composition, i.e. methyl-5-(2,4-dichlorophenoxy)-2-nitrobenzoate, is known and has been approved by various authorities as a selective herbicide during the last decade; it is disclosed, for example, in U.S. Pat. Nos. 3,652,645 and 3,776,715 and has the formula (1)

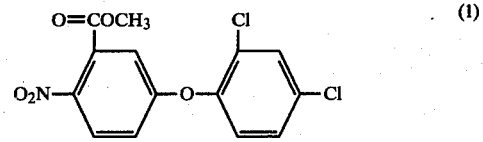

The non-proprietary or common name approved by ANSI and WSSA for this compound is "Bifenox" and this name, or the term "constituent (1)", will be used herein.

Constituent (2) of the inventive composition, i.e. 3-(3,4-dichlorophenyl)-1-methoxy-1-methyl urea, is known and has been approved as a selective herbicide for various crops during about two decades; it is disclosed, for example, in U.S. Pat. Nos. 2,960,534 and 3,079,244 and has the formula (2)

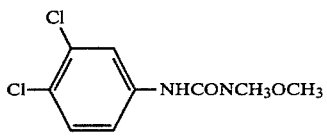

The common name approved by ISO, BSI and WSSA for this compound is "Linuron" and this name, or the term "constituent (2)", will be used herein.

Both constituents (1) and (2) are available, and can be used herein, in commercially available forms; conventional particle sizes of below 30 μm, notably 10 μm or smaller, of both constituents are preferred in the final compositions for many uses.

Constituent (3) of the inventive composition is a mineral oil, such as "white oil" and similar substantially non-volatile refined petroleum fractions of the type conventionally used in agrochemistry; essentially paraffinic hydrocarbon oils are preferred and numerous products including "white oil" are available commercially as essentially inert spray oils. Examples and parameters of mineral oils suitable for the invention are given, for example, in the "Pesticide Manual" (edited by H. Martin and C. R. Worthing, issued by the British Crop Protection Council), 4th Edition (1974), page 397.

Suitable mineral oils will boil, under normal pressure, at temperatures of above 200° C., preferably above 250° C., e.g. at 300° C. or more. Conventionally, such oils are graded according to the size of the fraction distilling at normal pressure and a given temperature. For example, at 336° C. (normal pressure), 64 to 79%, by volume, of a light grade mineral oil will distill, 40 to 49%, by volume, of a medium grade mineral oil will destill and 10 to 20%, by volume, of a heavy grade mineral oil will distill, and all three grades, per se or in mixture, can be used according to the invention. "Essentially paraffinic" with reference to mineral oil indicates that non-paraffinic constituents, if present, constitute a minor portion only, e.g. less than 10%, by weight.

While the amounts of the various constituents in the synergistic combination according to the invention can be varied within relatively wide limits, the weight ratio Bifenox:Linuron should generally be in the range of from about 1:6.25 to about 6.25:1 and preferably in the range of from 1:2.3 to 3.6:1. The mineral oil or constituent (3), on the other hand, should be present in an amount having a minimum volume, expressed in liters, that corresponds at least approximately to the total weight of Bifenox plus Linuron, expressed in kilograms; the amount of constituent (3) in a synergistic composition may be increased up to about 3.5 times the minimum amount.

Expressed in a general weight ratio, a preferred synergistic composition according to the invention includes about 0.75 to about 3.2 parts by weight of constituent (3) per each part by weight of the combined total of constituents (1) plus (2).

Typically, a maximum effectiveness about ten days after spraying is considered acceptable for controlled pre-harvest desiccation of potato crops and this can be achieved, according to the invention, with the following dosages, expressed in kilograms per hectare (kg/ha), of the essential constituents (1), (2) and (3) when applying them as an aqueous spray and taking into account the normal ranges of variables, such as planting density, degree of foliation, etc.:

constituent (1): about 0.4 to about 2.5 kg/ha, preferably 0.44 to 1.8 kg/ha;
constituent (2): about 0.4 to about 2.5 kg/ha, preferably 0.5 to 1 kg/ha;
constituent (3): about 1.6 to about 3.6 kg/ha, preferably 2.2 to 3.0 kg/ha (or, in terms of volume: about 2 to 4 liters/ha, preferably 2.8 to 3.2 liters/ha).

In situ concentrations or dosages in terms of weight of active ingredient per crop area may be varied to accelerate or delay the time of maximum effectiveness but an extremely fast effectiveness, say maximum desiccation within less than a week, is believed to be contrary to the concept of an environmentally acceptable defoliant/desiccant for pre-harvest use.

The optional but generally preferred constituent (4) includes at least one emulsifying agent and this term is used herein to refer to surface-active agents of the type known in agrochemistry for preparing stable and/or emulsifiable compositions that contain an oily constituent as an essential component and that are intended for use after dilution of the oily concentrate with a liquid aqueous diluent, e.g. normal water. Many suitable emulsifiers for agrochemical compositions of various types are obtainable commercially and emulsifiers of various categories can be used herein, e.g. alcanol amines of fatty acids, polyglycol ethers and the like, and numerous other examples will be found in standard reference books, e.g. "McCutcheon's Detergent and Emulsifier Annual" or "Encyclopedia of Surface-Active Agents" by Sisley and Wood.

The main function of optional constituent (4) is to prevent phase-separation of a concentrate and/or of a diluted aqueous spray material. Accordingly, selection of optimal components for constituent (4) may depend upon the formulation of the inventive composition. For example, when the inventive composition is a concentrate capable of storage, phase-separation for periods of months to one or two years may be desirable while a diluted spray composition requires stability for a relatively short period only, e.g. typically about 24 hours. It will be appreciated, however, that emulgation for a limited period can be obtained by mechanical means, e.g. high-shear mixing, so that constituent (4) is not believed to be critical for the invention but is generally preferred for ease of handling and application.

Generally, a preferred inventive composition contains constituent (4) to prevent phase-separation of both the concentrate as well as a diluted aqueous spray material prepared therefrom so as to satisfy the above mentioned stability requirements. Typically, constituent (4)—that may but need not be a mixture of different emulsifying agents—will constitute a minor weight portion of a concentrate, e.g. from about 0.1 to about 10%, by weight, depending upon the amount of mineral oil (3) and the desired stability parameters.

Further, compositions according to the invention may include conventional additives, adjuvants and the like constituents—therein below summarized as constituent (5)—depending upon the formulation and the intended type of use of the inventive composition. Again, such additives and their use are well known in the agrochemical art and include solvents, surfactants, thickening agents, defoaming agents, adhesion-improving agents, dispersing agents, anti-freeze agents, coloring materials, etc. Selection may depend upon the type of formulation, i.e. concentrate or spray; preferably, a concentrate includes most or all adjuvant constituents or additives (5) desired in the spray but admixture of specific adjuvants or additives (5) may be effected just prior to spraying.

Many preferred concentrated forms of the inventive composition will include an aqueous portion and be in the form of a concentrated emulsion capable of storage without phase-separation for at least about a year; stabilization may include prevention of sedimentation of the particulate solids by conventional dispersing agents depending upon the particle size of the solid constituents.

Accordingly, the term "constituent (5)" includes polyfunctional mixtures, e.g. a mixture of water, dispersing agent, thickener, adhesive, etc.

In a generally preferred form, the inventive composition is a fluid or semi-fluid composition suitable for dilution with water prior to use, e.g. in the form of a paste or of an emulsion concentrate, but other formulations might be used. The absolute concentrations of the constituents (1), (2) and (3) in a given composition depend essentially upon the type of formulation or use, i.e. a concentrate may consist of a major or even predominant portion of constituents (1), (2), (3) plus optionals (4), (5) while the sprayable or diluted form actually used for controlled pre-harvest defoliation or desiccation generally contains a fraction of a percent, by weight, to a few percents, by weight, say 0.1 to 5%, by weight, of the constituents just mentioned dispersed or emulsified in water.

Inventive compositions can be obtained by conventional blending, mixing or emulsifying methods from the above constituents, including milling in hammer mills, high-shear mixers, fluid mills and the like. As will be apparent from the above explanation of the essential and optional constituents of inventive composition and preparation methods, the present invention is based essentially upon a particular novel combination of prior art materials and the surprising synergism of the novel combination of constituents (1), (2) and (3) as explained in more detail below.

It has been found according to the invention, as evidenced by comparative field tests, that when applying the above constituents at the above rates, desiccation results are achieved that are fully equivalent to those obtained by prior art treatment with 8 kg/ha of DNOC or 1.65 kg/ha of Dequat, based upon evaluation 15 days after treatment. Prior art desiccants, such as DNOC and Dequat, tend to have a relatively fast desiccant action indicating a relatively drastic biological effect and test results indicate that the composition according to the invention clearly has a less drastic effect upon plant biology; this, in turn, seems to confirm that the composition according to the invention provides for less disturbance of environmental conditions.

The less drastic effects of inventive compositions is in line with the fact that all constituents of a synergistic composition according to the invention are substantially less toxic than comparable active ingredients according to the art. While acute toxicity as evidenced by animal test is of limited value when judging substances for agrochemical use, such values are indicative of handling and use advantages of the synergistic composition according to the invention and the following toxicity values ($LD_{50}$ per os, rats) of the various active ingredients according to the invention and according to the art are given to illustrate this:

Bifenox: >6400 mg/kg,
Linuron: 4000 mg/kg,
DNOC: 20–40 mg/kg,
Dinoseb: 58 mg/kg,
Diquat: 231 mg/kg.

Keeping in mind that high $LD_{50}$ values indicate low toxicity it is apparent that the chemicals used in the inventive combination are less toxic by one or two orders of magnitude.

Field test results obtained with inventive compositions as potato desiccants show that their use does neither impair the quality of the harvested potatoes nor that residues will remain in the soil. Accordingly, it is expected that the invention provides for controlled defoliation/desiccation that is substantially less detrimental to the environment than prior art compositions. This is substantiated by the fact that the chemicals contained in the inventive synergistic composition have been tested per se for prolonged periods by various Institutes and authorities and are admitted and acknowledged as comparatively safe herbicides.

As regards synergism of the combination that characterizes the invention it is to be emphasized that each constituent (1), (2) and (3), taken per se, is neither suitable for foliage reduction or foliage elimination in general nor suitable for desiccation of potato shrubbs in specific and the advantageous effects of the combination can be explained only by an unexpected synergysm. This is substantiated by the results of typical field tests summed up as follows:

The results of parallel greenhouse and field tests (made as explained in more detail below) show that the application of Bifenox per se at a rate of 0.44 kg/ha results in a reduction of above-ground plant parts (foliage and stems) of potato plants of only 32.5%; the same rate of Bifenox plus 3 liters of mineral oil gave a somewhat improved distribution and resorption of the Bifenox resulting in a 85% improvement of the treatment effect. When quadrupling the application rate of Bifenox (without mineral oil), an effectiveness of only 75% was observed.

A similar synergism is apparent from tests with Bifenox plus Linuron. Linuron per se has no effectiveness whatsoever when applied at a rate of 0.5 kg/ha. With the same rate of Linuron plus Bifenox at a rate of 0.88 kg/ha, an effectiveness of 65% was observed; when quadrupling the Bifenox rate combined with Linuron, no further increase of effectiveness was observed Test and evaluation methods were as follows:

Greenhouse Tests

Potato tubers were planted in plastic pots of 20 cm diameter filled with sandy loam soil. Three tubers were arranged about 3 cm below the soil surface in each pot. The pots thus planted were placed in a greenhouse at 20° to 22° C. and watered as necessary. The plants were allowed to reach a height of 30 to 35 cm and the number of sprouts per tuber was reduced to two prior to the tests. A laboratory sprayer having a single fan jet nozzle operating at a pressure of 3 bar and at an output of about 1000 liters/hectare was used for test spraying.

Evaluation Method and Scale

Test plants were observed 5, 10 and 15 days after treatment. Foliage kill/desiccation observed was evaluated as follows:

| percent of foliage kill/desiccation | numeric value for evaluation |
|---|---|
| 0 | 1 |
| 32.5 | 2 |
| 65 | 3 |
| 75 | 4 |

-continued

| percent of foliage kill/desiccation | numeric value for evaluation |
|---|---|
| 85 | 5 |
| 90 | 6 |
| 95 | 7 |
| 97.5 | 8 |
| 100 | 9 |

Each evaluation was made in blocks of three replicates.

Field Tests

A total of three replicated trials was carried out in different regions of Switzerland and on different soil types. The materials under test were applied at a rate equivalent to 1200 liters of water per hectare using a pressure of 3 bars. A field plot sprayer (Van der Weij, "AZO") was used and plots of 10 m² each with randomized block designs were used for the replicates. The materials tested were applied just prior to (about 7–10 days) or at the start of normal senescence of the potato foliage and stems (normally around mid-August).

Desiccation of foliage and stem was observed 2, 8, 10 and 15 days after spraying, using the above described 1 to 9 evaluation scale wherein the numeric value of 1 is no desiccation, while 9 corresponds with 100% desiccation.

Results

Results of tests summarized in Table I indicate that the essential constituents of the synergistic combination do not per se, or in sub-combinations, have an appreciable defoliating/desiccant effect. Commercial white oil was used as constituent (3).

TABLE I

| Constituent | Dosage rate, kg/ha (liters/ha where indicated | Foliage kill/desiccation in greenhouse test, potatoes (scale 1 to 9 | | |
|---|---|---|---|---|
| | | 5 | 10 | 15 (days after treatm.) |
| (1) | 1.76 | 3 | 4 | 3 |
| (1)] | 1.76 | 3 | 3 | 3 |
| (2)] | 0.5 | | | |
| (1) | 0.88 | 2 | 2 | 2 |
| (1)] | 0.88 | 2 | 3 | 2 |
| (2)] | 0.5 | | | |
| (1) | 0.44 | 2 | 2 | 2 |
| (1)] | 0.44 | 2 | 2 | 2 |
| (2)] | 0.5 | | | |
| (2) | 0.5 | 1 | 1 | 1 |
| (2) | 0.75 | 1 | 1 | 1 |
| (3) | — | 1 | 1 | 1 |
| (1)] | 1.76 | 6 | 5 | 4 |
| (3)] | 3 (liters) | | | |
| (1)] | 0.88 | 5 | 5 | 4 |
| (3)] | 3 (liters) | | | |
| (1)] | 0.44 | 5 | 5 | 3 |
| (3)] | 3 (liters) | | | |
| (3) | — | 1 | 1 | 1 |

The results of the tests with constituent combinations according to the invention believed to be representative are summarized in Tables II and III (synergism of the combination (1)+(2)+(3)); Table II shows mean values of defoliant/disiccant effect (leaf and stem):

TABLE II

| Constituent combination | Dosage rate, kg/ha (liters/ha where indicated) of constituents | Mean defoliation/desiccant effect (potato) of combination (days after treatment) | | | |
|---|---|---|---|---|---|
| | | (2) | (8) | (10) | (15) |
| (1) | 1.76 | 3.5 | 6.6 | 8.8 | 9 |
| (2) | 0.5 | | | | |

TABLE II-continued

| Constituent combination | Dosage rate, kg/ha (liters/ha where indicated) of constituents | Mean defoliation/desiccant effect (potato) of combination (days after treatment) | | | |
|---|---|---|---|---|---|
| | | (2) | (8) | (10) | (15) |
| (3) | 3 (liters) | | | | |
| (1) | 0.88 | 3.7 | 6.3 | 8.5 | 9 |
| (2) | 1 | | | | |
| (3) | 3 (liters) | | | | |
| (1) | 0.88 | 2.6 | 5.7 | 7.7 | 8.7 |
| (2) | 0.5 | | | | |
| (3) | 3 (liters) | | | | |

Table III shows differentiated values of defoliant/desiccant effect of inventive compositions on leaves (L) and haulm (H) of the potato plants:

TABLE III

| Constituent combination | Dosage rate, kg/ha (liters/ha where indicated) of combination | Specific defoliation/desiccant effect (potato) of combination (days after treatment) | | | | | |
|---|---|---|---|---|---|---|---|
| | | (2) | | (8) | | 110) | |
| | | L | H | L | H | L | H |
| (1) | 1.76 | 5 | 2 | 7.5 | 5.8 | 9 | 8.5 |
| (2) | 0.5 | | | | | | |
| (3) | 3 (liters) | | | | | | |
| (1) | 0.88 | 5 | 2.5 | 7.5 | 5 | 9 | 8 |
| (2) | 1 | | | | | | |
| (3) | 3 (liters) | | | | | | |
| (1) | 0.88 | 4 | 1.5 | 6.5 | 4.9 | 8 | 7.5 |
| (2) | 0.5 | | | | | | |
| (3) | 3 (liters) | | | | | | |

The following non-limiting examples are given to further illustrate the invention. Parts are by weight unless indicated otherwise.

EXAMPLE I 907 g of Bifenox (commercial product, purity of 97% by weight) and 526 g of Linuron (commercial product, purity of 95%) were preblended in a hammer mill. While still in the hammer mill, 3,5 liters of water were added. Milling was continued until the particle size of the solids were decreased to below about 10 μm.

250 g of a mixed anion active and non-ionic emulsifier (product "Atlox 4853 B" of Atlas Chemical Industries N.V.) were added to the resulting mix and 3 liters of white oil ("Spray Oil 11E" of Sun Oil Corp.) were emulsified in the mix. The product obtained was a fluid paste.

7 (±1) liters of the paste obtained were dispersed in 500 to 1500 liters of water to obtain spray compositions. The amount of water used for dilution can be varied to meet the requirements of the spraying apparatus. The spray composition was used for desiccation of a potato plant culture about two weeks prior to normal senescence. Application rates of the essential constituents were as follows:

(1) Bifenox: 0.88 kg/ha,
(2) Linuron: 0.5 kg/ha,
(3) white oil: 3 liters/ha.

15 days after treatment, a substantially complete desiccation (leaves and stem) of the potato plants is observed.

EXAMPLE II

Example I was repeated with the exception that the constituents (1), (2) ratio was changed for application of
(1) Bifenox: 1.76 kg/ha,
(2) Linuron: 0.5 kg/ha,
(3) white oil: 3 liters/ha,
as a potato desiccant.

Substantially complete desiccation of the potato plants was observed 10 days after treatment.

EXAMPLE III

Example I was repeated with the exception that the constituents (1), (2) ratio was changed for application of
(1) Bifenox: 0.88 kg/ha,
(2) Linuron: 1.0 kg/ha,
(3) white oil: 3 liters/ha,
as a potato desiccant. Substantially the same result as in Example II were obtained.

EXAMPLE IV (A) 55 parts of Bifenox and 32 parts of Linuron (both of commercial grade purity) were preblended in a hammer mill for reduction of particle sizes to <1 mm; the result is batch (A).

(B) In a separate operation, 187 parts of white oil (same as in Example I) were mixed by stirring with commercially available emulsifying agents supplied by Atlas Chemical Industries N.V., i.e. 2 parts of emulgator "EL 4000" and 5 parts of emulgator "3425 F"; the result is batch (B).

(C) 13.5 parts of a mixture of commercial herbicide adjuvants consisting of 2.5 parts of an extremely fine silicon dioxide, 10 parts of a dispersant ("Supragol," registered trademark) and 1 part of at thickening agent or adhesive on polysaccharide basis ("Rodopol," registered trademark) were admixed with 254 parts of water; the result is batch (C).

Batch (B) was added to batch (A) in the hammer mill to produce a dispersion of constituents (1), (2) in (3). Then, batch (C) was added to the dispersion in the hammer mill and milling was continued for emulgation and solid particle size reduction to below about 10 μm. The inventive product (concentrate) obtained could be stored.

When adding portions of from 1 to 10 parts of concentrate to water portions of from 100 to 2000 parts in conventional herbicide mix tanks, sprayable liquids of adequate stability for conventional application could be obtained.

EXAMPLE V

Soil samples were collected 4 to 5 weeks after operation of Examples I to III including harvesting of the potatoes; the samples were used in greenhouse tests to evaluate persistence by measuring the germination of wheat, barley, Alopecurus m. and oil seed rape as test plants. Completely normal germination and growth of wheat, barley and oil seed rape was observed indicating that no significant residue problems for following crops were to be expected.

Further, potatoes harvested after operation of Examples I to III were inspected. Neither vascular browning nor other indications of detrimental effects upon the potatoes were observed.

While particular examples have been given above for the inventive composition and the inventive method, it will be appreciated that both the defoliant as well as the desiccation aspect according to the invention is not limited to the pre-harvest treatment of potatoes but will be applicable to other important crops including soy beans, cotton or the like crops where pre-harvest defoliation is conventional for improved operation of harvesting machines.

In all such crops, controlled defoliation is expected to provide for the advantages known to be connected with selective removal of foliage prior to harvesting and/or to better synchronize crop maturation, but with a synergistic combination of substances which per se are known to be safe and would, if used singly or in subcombinations have no significant defoliant effect.

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. A composition suitable for controlled pre-harvest defoliation and/or desiccation of crop plants comprising, in a synergistic combination, the constituents:
   (1) methyl-5-(2,4-dichlorophenoxy)-2-nitrobenzoate;
   (2) 3-(3,4-dichlorophenyl)-1-methoxy-1-methyl urea; and
   (3) a mineral oil;
   said composition containing said constituents (1) and (2) in a weight ratio of from 1:6.25 to 6.25:1 and said constituent (3) being contained in said composition in an amount of from about 0.8 to about 3.2 parts, by weight, per each part, by weight, of the total amount of said constituents (1) and (2).

2. The composition of claim 1, wherein said weight ratio of constituents (1):(2) is in the range of from 1:2.3 to 3.6:1.

3. The composition of claim 1 additionally comprising an agrochemical emulsifying agent.

4. A method of controlled pre-harvest defoliation or desiccation of crop plant foliage and stem materials comprising applying onto said foliage and stem materials a synergistic combination of
   (1) methyl-5-(2,4-dichlorophenoxy)-2-nitrobenzoate in an amount of from 0.4 to 2.5 kg per hectare;
   (2) 3-(3,4-dichlorophenyl)-1-methoxy-1-methyl urea in an amount of from 0.4 to 2.5 kg per hectare; and
   (3) a mineral oil in an amount of from 1.6 to 3.6 kg per hectare.

5. The method of claim 1, wherein said combination further comprises an emulsifying agent and wherein said combination is applied as an aqueous spray.

6. The method of claim 4, wherein said constituents of said combination are applied onto a crop area at a rate of 0.44 to 1.8 kg of constituent (1) per hectare; 0.50 to 1.0 kg of constituent (2) per hectare; and 2.2 to 2.6 kg of constituent (3) per hectare.

7. A method of pre-harvest desiccation of foliage and stems of potato plants comprising the step of spraying onto said plants an aqueous formulation containing a synergistic combination of the constituents
   (1) methyl-5-(2,4-dichlorophenoxy)-2-nitrobenzoate in an amount of from 0.4 to 2.5 kg per hectare;

(2) 3-(3,4-dichlorophenyl)-1-methoxy-1-methyl urea in an amount of from 0.4 to 2.5 kg per hectare; and (3) a mineral oil in an amount of from 1.6 to 3.6 kg per hectare.

8. The method of claim 7, wherein said combination of constituents additionally includes an agrochemical emulsifying agent.

9. The method of claim 7, wherein said aqueous formulation contains said constituents in amounts to provide for a rate of spray application per hectare of 0.44 to 1.8 kg of constituent (1), 0.50 to 1.0

* * * * *